US007753886B2

(12) United States Patent
Vath et al.

(10) Patent No.: US 7,753,886 B2
(45) Date of Patent: Jul. 13, 2010

(54) MEDICINE DISPENSING SYSTEM

(76) Inventors: Frances R. Vath, 20058 State Route O, Rolla, MO (US) 65401; Max B. Vath, 20058 State Route O, Rolla, MO (US) 65401

( * ) Notice: Subject to any disclaimer, the term of this patent is extended or adjusted under 35 U.S.C. 154(b) by 210 days.

(21) Appl. No.: 12/016,568

(22) Filed: Jan. 18, 2008

(65) Prior Publication Data

US 2008/0177305 A1 Jul. 24, 2008

Related U.S. Application Data

(60) Provisional application No. 60/844,276, filed on Jan. 22, 2007.

(51) Int. Cl.
*A61M 1/00* (2006.01)

(52) U.S. Cl. ....................... 604/151; 604/140; 604/181; 606/234

(58) Field of Classification Search .................. 604/38, 604/93.01, 181, 183–185, 187, 214, 295, 604/911, 36–37, 131–132, 140–142, 151–153, 604/216–217, 222; 606/234–236; 222/94
See application file for complete search history.

(56) References Cited

U.S. PATENT DOCUMENTS

| | | | | |
|---|---|---|---|---|
| 652,034 | A | 6/1900 | Meinecke | |
| 1,518,823 | A | 12/1924 | Schmidt | |
| 2,824,561 | A | 2/1958 | Mueller | |
| 3,426,755 | A | 2/1969 | Clegg | |
| 3,610,248 | A | 10/1971 | Davidson | |
| 4,132,232 | A | 1/1979 | Lerner | |
| 4,896,666 | A | 1/1990 | Hinkle | |
| 5,123,915 | A * | 6/1992 | Miller et al. | 606/234 |
| 5,601,605 | A * | 2/1997 | Crowe et al. | 606/236 |
| 5,620,462 | A * | 4/1997 | Valenti | 606/234 |
| 5,843,030 | A * | 12/1998 | Van Der Merwe | 604/77 |
| 6,197,044 | B1 | 3/2001 | Clayton | |
| 6,454,788 | B1 | 9/2002 | Ashton | |
| 6,588,613 | B1 | 7/2003 | Pechenik | |
| 6,776,157 | B2 | 8/2004 | Williams | |
| 2003/0083696 | A1 | 5/2003 | Avital | |
| 2004/0124168 | A1 | 7/2004 | Silver | |

* cited by examiner

*Primary Examiner*—Nicholas D Lucchesi
*Assistant Examiner*—Theodore J Stigell
(74) *Attorney, Agent, or Firm*—Charles McCloskey

(57) ABSTRACT

A medicine dispensing pacifier has a centered nipple upon a guard and a reservoir communicating through the guard to the nipple. The reservoir, opposite the guard, has a cap, and upon removing it, a caregiver places medicine into the reservoir. Then the caregiver returns the cap to seal the reservoir. The infant then suckles the nipple, ingesting the medicine drawn from the reservoir. Alternately, the pacifier includes an air permeable membrane, a flexible cap, for dispensing medicine under pressure through a nipple into an infant that has difficulty taking medicine. The infant then suckles upon the nipple and the caregiver presses upon the cap raising the flow of medicine through the nipple into the mouth of the infant. The cap augments the natural suckling of the infant with pressure and without spilling medicine.

1 Claim, 3 Drawing Sheets

MEDICINE DISPENSING SYSTEM

CROSS REFERENCE TO RELATED APPLICATION

This non-provisional application claims priority to the provisional application Ser. No. 60/844,276 filed on Jan. 22, 2007 and is commonly owned by the same inventor.

BACKGROUND OF THE INVENTION

The medicine dispensing pacifier relates generally to infant care equipment and more specifically to a pacifier having a measured container thereon for supplying a certain quantity of medicines.

A unique aspect of the present invention is an integral receptacle, or reservoir, for dispensing fluid or crushed medicine through a nipple to an infant or infirm person of any age. The reservoir has a lip that connects with a nipple and it also connects to the guard of a pacifier. The nipple is in communication directly with the reservoir for dispensing medicine. In suckling the nipple, an infant draws in the medicine, at a known dosage, through an aperture in the nipple and then into the infant's mouth. The nipple is oval and shaped to fit within an infant's mouth. The present invention emulates the nipple shape an infant encounters during breast feeding while simultaneously providing medicine.

Babies, or infants, are also inclined to cry as a way of notifying parents of their needs. At times, the cry of an infant is inappropriate and inconvenient. Parents seek ways to pacify their infants and restore some tranquility to a home or other environment. Also, infants have the instinct to suckle milk from their mothers. Following the suckling instinct, infants will suckle almost anything placed into their mouths particularly items having a nipple shape. When suckling, an infant has a difficult time crying. Pacifiers having a fake nipple are accepted by infants and satisfy the infant, for a time. Also, pacifier use is associated with a significant decrease in sudden infant death syndrome.

Pacifiers generally have three parts: a nipple upon which the infant suckles, a base, or guard, upon which the nipple attaches, and a tab, or ring, extending from the base that the caregiver can grasp. Many pacifiers through the years have had solid nipples.

A pacifier of any design, whether it be the hollow type that may have air pressure provided within its interior, because it has apertures, or even the solid nipple, induces the infant to suckle. When an infant undertakes that type of activity, it creates a vacuum in the mouth due to the constant sucking pressure. This oral cavity vacuum then withdraws medicine from the medicine reservoir for ingestion by the infant. In addition, since the mouth cavity is accessible to the nasal cavity, and the ear passages, the vacuum may also draw medicine into those areas of the head. The various intra-oral passages often succumb to infection within the ear canals and ear fluid accumulation, and other maladies. Some of these maladies and discomforts respond to medicine delivered orally to an infant.

DESCRIPTION OF THE PRIOR ART

Various nipples and bottle designs over the years have adjusted the effects of suckling upon an infant. An early patent to Meinecke, U.S. Pat. No. 652,034, is upon a nipple holder, circa 1900. The '034 patent shows a nipple that appears to be hollow, and then mounts upon a nut that has threadily engaged therein a handle that incorporates a T-vent. This nipple holder, has a venting structure, but does not define a medicine reservoir.

The patent to Schmidt, et al, U.S. Pat. No. 1,518,823, shows a combination nipple and pacifier, and the nipple shows an aperture, for allowing fluids to be emptied from the accompanying nursing bottle. But, when the nipple is applied or threadily engaged into the pacifier, particularly the blind bore, it has no ability to vent. Hence, this pacifier was not designed for supplying medicine.

The patent to Mueller, U.S. Pat. No. 2,824,561, shows a combination infant pacifier and feeding device. This particular pacifier describes a longitudinal bore, in combination with the plastic tube, that equalizes air pressure in the pacifier body, and this device is more involved with the filling of the pacifier body, such as with syrup, honey, or the like, and then closed with a stopper. The description mentions little about the pacifier body receiving medicines of a certain amount.

The patent to Clegg, U.S. Pat. No. 3,426,755, shows a pacifier, used as a medicine feeder. This pacifier has a tube connected within a ring behind the guard of a pacifier. The tube connects opposite the guard to a medicine dropper where compression of the dropper moves medicine through the tube to a nipple. As the ring has an opening for the tube, the ring does not contain medicines placed therein as in the present invention.

The patent to Davidson, U.S. Pat. No. 3,610,248, shows a gum exercise device. This is not just a pacifier, but has a cavity within the nipple that has a series of apertures therein, and with the nipple being filled with a hydrophilic plastic material. This patent describes a nipple filled with material through which passes medicines from the cavity. The present invention though omits hydrophilic material and attaches a reservoir for viewing medicinal contents supplied to a hollow nipple.

The patent to Lerner, U.S. Pat. No. 4,132,232, shows an integrally molded pacifier for infants. But, it does contain a variety of apertures, so that if the pacifier is inadvertently swallowed, the infant will still be able to breathe. But this pacifier does not provide storage for medicine.

The patent to Hinkle, U.S. Pat. No. 4,896,666, shows a face mask assembly and pacifier that tightly contacts the face of the wearer, and is more useful than being used for nipple purposes, such as during preoperative procedures, when anesthetics are applied. While the pacifier does have at least one aperture therein, this particular aperture functions as a passageway to allow medical gas therethrough.

The patent to Clayton, U.S. Pat. No. 6,197,044, shows a feeding system and apparatus for infants. While this device defines an improved pacifier, having the usual nipple and mouth guard, the nipple incorporates an inner lumen that is configured to removably receive a tubular member which provides a passageway for oral fluids to enter into the infant.

The patent to Ashton, U.S. Pat. No. 6,454,788, discloses a method and apparatus for oral hydration and medication administration using a pacifier. This apparatus includes a nipple and shield, but incorporates a refillable reservoir, apparently for medication administration. It does incorporate a number of fluid-flowing physiologic gutters for forwarding medication and medical fluids adjacent to the tongue of the user to avoid stimulating the gag reflex. This particular device further includes an access assembly that is removably attached to a flange, and a detachable reservoir for holding liquids that connects to the device through a tube to the neck of the device, for delivering and administering liquids through the nipple to an infant or young child. This patent appears a modern version of that of Clegg's U.S. Pat. No. 3,426,755.

The patent to Pechenik, et al., U.S. Pat. No. 6,588,613, shows an infant-feeding nipple, not just a pacifier per se. This device defines a nipple for use with an infant bottle unlike the present invention and that delivers water-based fluids to the child through the nipple. This device also may collapse during usage.

The patent to Williams, et al., U.S. Pat. No. 6,776,157, is upon a medical pacifier and method for use thereof for the induction of anesthesia and other gases to an infant. This device has a hollow nipple upon a base that includes a breathing tube extending through both. The breathing tube allows for inhalation of supplied gases and exhalation from a pediatric patient. The breathing tube though does not permit storage of liquid medicine therein and this device may collapse as well during usage.

The published application to Silver, No. US 2004/0124168, is upon an artificial nipple of integrated structure, for feeding purposes, and apparently has a snap engagement onto a container. The engagement is achieved through its arrangement of grooves and lips. This invention from Silver does not serve as an improved feeding nipple and when it is radially compressed, it does not allow the passage of any fluid therethrough.

Finally, the published application to Avital, No. US2003/0083696 is a standard pacifier, but the back end of its tube section is completely opened for full access to the atmosphere.

The present invention overcomes the difficulties of the prior art. The present invention has an air tight reservoir that secures to a guard at the base of a hollow nipple. The reservoir includes gradations and a known size to allow for dispensing of precise doses of medicinal fluids and dissolved medicinal solids through the aperture of a nipple. The reservoir detaches from the guard for filling by the caregiver of an infant. The infant ingests the medicines from the reservoir through suckling upon the hollow nipple.

The present invention, unlike the prior art, provides means for loading a certain amount of medicine into a pacifier for an infant to suckle while ingesting the medicine with a minimum of fussiness. The infant need not stretch its mouth or move its tongue to receive medicine from a dropper or other device. The infant can orient the present invention in any direction but down and still receive medicine. The infant does so by grasping the nipple with its gums and nascent teeth and suckling upon the nipple which lowers the pressure of the intra-oral cavity so that the medicine is drawn out of the reservoir into the infant's mouth.

SUMMARY OF THE INVENTION

The medicine dispensing pacifier has a nipple centered upon a guard and a reservoir communicating through the guard to the hollow nipple. The reservoir, opposite the guard has a screw on cap that removes for placing medicine into the reservoir. Upon removing the cap, a caregiver pours, places, or spoons medicine into the reservoir. Then the caregiver returns the cap onto the reservoir thus sealing the medicine into the pacifier. The infant then suckles the nipple, ingesting the medicine drawn from the reservoir. There has thus been outlined, rather broadly, the more important features of the invention in order that the detailed description thereof that follows may be better understood and that the present contribution to the art may be better appreciated.

Alternately, the pacifier includes a flexible cap, such as silicone, for infants that encounter difficulty when taking medicine and suckling. As above, the cap screws on to a reservoir. In usage, the cap is removed and the medicine placed within the reservoir as before. The caregiver then returns the cap upon the reservoir and seals in the medicine. The infant then suckles upon the nipple and the caregiver presses upon the cap boosting the flow of medicine through the nipple into the mouth of the infant. The cap augments the natural suckling of the infant with external pressure and without spillage of the medicine.

The present invention includes various sizes for various ages of infants and various shaped nipples to suit the preferences of infants. The present invention also has reservoirs of predetermined volumes to allow for filling and dispensing of precise dosages of medicine. The reservoirs can be filled by medical staff, pharmacy staff, and caregivers as needed. The pacifier can be made of materials and constructed at a low cost suitable for being disposable. Additional features of the invention will be described hereinafter and which will form the subject matter of the claims attached.

Numerous objects, features and advantages of the present invention will be readily apparent to those of ordinary skill in the art upon a reading of the following detailed description of the presently preferred, but nonetheless illustrative, embodiment of the present invention when taken in conjunction with the accompanying drawings. Before explaining the current embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, the phraseology and terminology employed herein are for the purpose of description and should not be regarded as limiting.

One object of the present invention is to provide a new and improved medicine dispensing pacifier.

Another object is to provide such a medicine dispensing pacifier that stores and dispenses a certain dose of medicine to an infant, or an infirm person of any age.

Another object is to provide such a medicine dispensing pacifier that has a low cost of manufacturing so the consuming public can readily purchase the medicine dispensing pacifier through existing retail outlets.

These together with other objects of the invention, along with the various features of novelty that characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated a preferred embodiment of the invention.

BRIEF DESCRIPTION OF THE DRAWINGS

In referring to the drawings.

The same reference numerals refer to the same parts throughout the various figures.

DESCRIPTION OF THE PREFERRED EMBODIMENT

Figure 1:
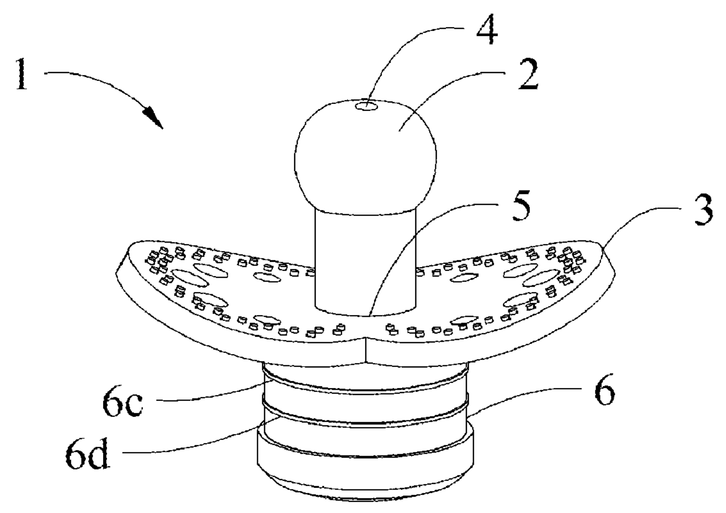
FIG. 1 illustrates a bottom view of the present invention.

The present invention overcomes the prior art limitations and provides a medicine dispensing pacifier for infants and alternately infirm persons of any age. The preferred embodiment of the present invention 1, shown in FIG. 1, has a nipple 2 generally perpendicular to a guard 3. The nipple is generally hollow and has a bulbous end opposite the guard. The bulbous end has an aperture 4 generally centered in the bulbous end to allow for the free flow of medicines or other fluidized matter. Opposite the bulbous end, the nipple has a mouth 5 that abuts the guard. The mouth has slightly less width than the maximum extent of the bulbous end. The mouth then joins to the guard and provides fluid communication through the guard.

The guard 3 is substantially planar, though here shown embodied as partially curved. The guard has a shape to fit an infant comfortably while preventing the infant from ingesting the nipple. In this embodiment, the guard has a plurality of holes therethrough for decorative purposes. In alternate embodiments, the guard is of solid construction. In the preferred embodiment, the guard curves inwardly with the nipple upon the interior of the guard. Opposite the nipple, the present invention has the reservoir 6. The reservoir is generally cylindrical in shape with a closed bottom 6*a* and an opposite mouth or lip. The reservoir connects to the guard in proximity to the lip 7. The reservoir has a known volume, such as one teaspoon, one tablespoon, or their metric equivalents, that can be filled with medicines of various kinds for dispensing through the hollow nipple and the aperture and into the infant. The reservoir can be prepackaged with over the counter medicines or prescriptions for retail at a pharmacy or other store.

Figure 2:
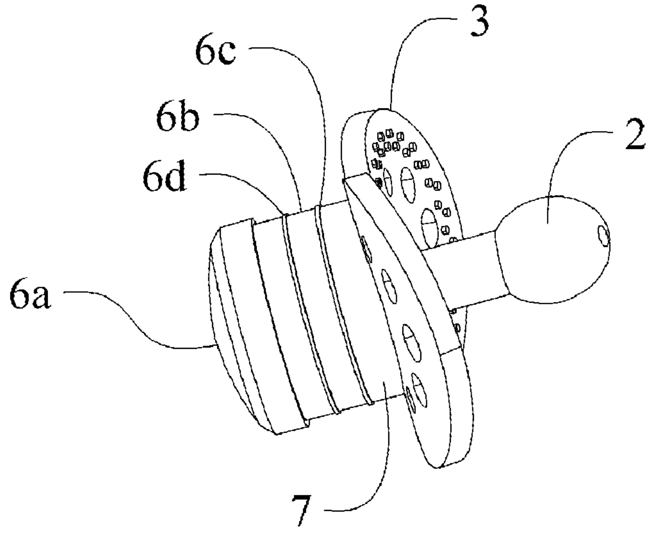
FIG. 2 shows a side view of the present invention.

Turning the medicinal pacifier, FIG. 2 shows a side view of the preferred embodiment of the invention. As before, the nipple 2 is located upon the interior of a curved guard 3. The nipple has its bulbous end opposite the reservoir 6. The nipple connects to a central opening in the guard and receives fluids from the reservoir opposite the guard. The reservoir 6 has a closed bottom 6*a* and a perimeter wall 6*b* that contain fluids, typically pediatric medicines. The wall is generally round and of a height similar to the diameter of the reservoir. The wall has at least one gradation, as at 6*c*, printed or etched upon the perimeter. The gradation identifies the volume of medicine contained within the reservoir or alternatively the maximum volume. The gradation is located for convenient visibility by a caregiver. This figure also shows a second gradation, as at 6*d*, showing the midpoint in volume between the maximum volume and an empty reservoir. The midpoint gradation aids a caregiver regarding how much medicine or time remains until the reservoir empties. Above the maximum gradation and opposite the bottom, the reservoir has a lip 7. The lip is generally round and connects the reservoir to the guard and allows for removal and reconnection of the reservoir to the guards. The lip permits reuse of the reservoir as during a multiple dosage course of medicine. The lip also permits filling of the reservoir at a pharmacy with a medicine and then providing of a filled pacifier as a prescription item.

Figure 3:
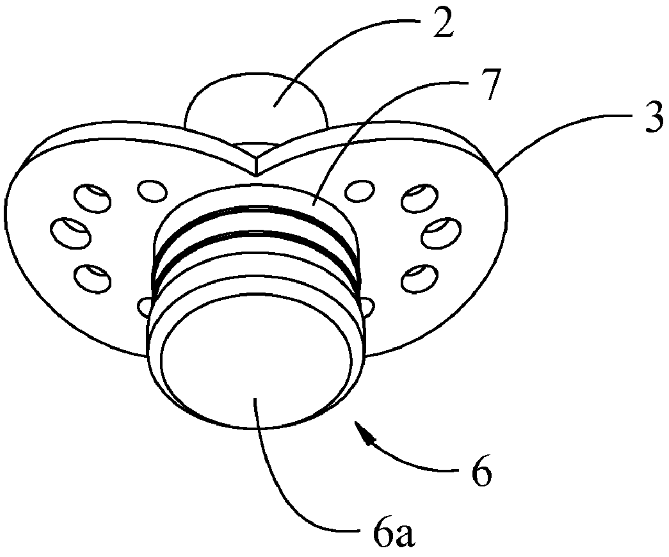
FIG. 3 shows an end view of the invention with the medicine reservoir in the foreground.

FIG. 3 then shows the medicinal pacifier from the end proximate the bottom 6*a* of the reservoir 6. The reservoir is generally cylindrical with a closed, preferably flat, bottom. The flat bottom allows the pacifier to be stood upright for filling at a pharmaceutical factory or retail pharmacy among other locations. The flat bottom also allows a caregiver to stand the pacifier upright and locate the nipple away from other undesirable surfaces. Opposite the bottom, the reservoir connects with the lip 7 to the proximate center of the guard 3. The lip is generally round and of slightly less diameter than the reservoir. The reservoir gently tapers opposite the bottom above the wall 6*b* to connect with the lip. The lip has a diameter generally less than the width of the guard so that the reservoir blends somewhat with the outward appearance of the guard. Opposite the lip, the mouth of the nipple connects with the guard so that medicines may pass from the reservoir into the nipple and then to the infant.

Figure 4:
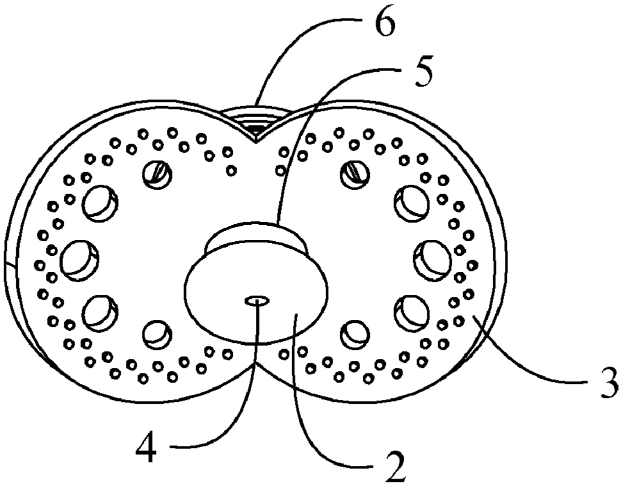
FIG. 4 shows an end view opposite that of FIG. 3 with the nipple in the foreground; and, FIG. 5 describes an exploded view of the invention with alternate caps for the medicine reservoir.

FIG. 4 shows the opposite view of FIG. 3. Here the nipple 2 is in the foreground with the aperture 4 generally centered in the bulbous end. The hollow nipple tapers in width behind the bulbous end towards the guard 3. Upon the guard, the mouth 5 of the nipple communicates through an opening in the guard to the reservoir in the background of this figure. In a further alternate embodiment, the reservoir has an air permeable membrane opposite the bottom that allows for venting through the nipple and for dispensing of medicine through another aperture in the membrane. During suckling, the partial vacuum created by the infant draws medicine from the reservoir through the other aperture while replacement air passes through the membrane and into the reservoir thus allowing for free flow of medicine.

Figure 5:
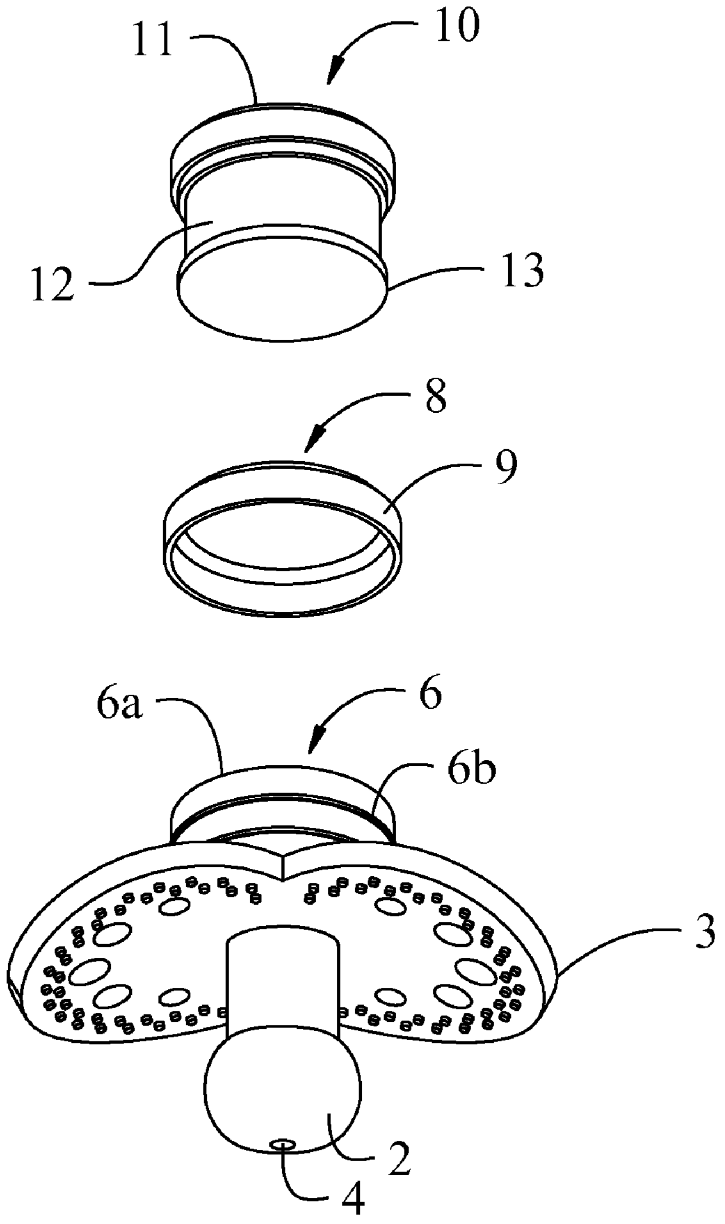

An alternate embodiment of the present invention is shown in FIG. 5. The alternate embodiment has a nipple 2 behind an aperture 4 that connects with a guard 3 as before. Opposite the nipple, the guard has a reservoir 6 having a generally hollow form with a wall 6*b* connecting to the guard but without a bottom. Opposite the guard, the wall of the reservoir can receive a pump to assist the dispensing of medicine from the reservoir into the nipple. One pump is a flexible cap 8, generally silicone with a rim 9. The cap has a convex shape and the rim has an inner diameter similar to that of the outer diameter of the reservoir. Fitting the cap upon the rim, a caregiver presses upon the cap, and pressurizes the reservoir briefly to force medicine from the reservoir through the nipple into the infant. A further alternate embodiment has a pump that compresses the content of the reservoir. As before, the reservoir is hollow with a wall 6*b* and no bottom. The reservoir receives a plunger 10 that has a convex dome like cap 11 upon a base 12 with a diameter similar to the inside diameter of the reservoir. In use, a caregiver, or pharmacist, holds the pacifier nipple downwardly with the reservoir upward. The caregiver then loads a measured amount of medicine into the reservoir and placed the base 12 within the wall 6*b* of the reservoir so that the cap 11 is outwardly from the guard. The base has a perimeter flange 13 that prevents medicine from leaking out of the plunger when pressed into the reservoir. The caregiver then places the nipple into an infant's mouth and presses the cap to dispense medicine with some pressure from the reservoir and through the nipple into the infant.

A generally straight nipple with a bulbous end has been described. Alternatively, the nipple deviates upward, or superiorly, near the guard towards the wall of the reservoir and then slightly downward, or inferiorly, at the free end of the nipple opposite the guard. This slightly curved nipple mimics the human breast anatomy an infant encounters during feeding.

From the aforementioned description, a medicine dispensing pacifier has been described. The medicine dispensing pacifier is uniquely capable of dispensing a known volume of medicine from a reservoir through a nipple into an infant. The medicine dispensing pacifier and its various components may be manufactured from many materials, including but not limited to, polymers, polyvinyl chloride, high density polyethylene, polypropylene, nylon, and composites. The pacifier may have a variety of sizes for infants of various ages and be provided in various colors.

As such, those skilled in the art will appreciate that the conception, upon which this disclosure is based, may readily be utilized as a basis for the designing of other structures, methods and systems for carrying out the several purposes of the present invention. Though liquid medicines have been described, powdered and dissolved medicines, and powdered and dissolved foods are also foreseen as applications for this invention. Though usage of the invention with infants is preferred, the invention can also be used with people, particularly the infirm, of all ages. Therefore, the claims include such equivalent constructions insofar as they do not depart from the spirit and the scope of the present invention.

We claim:

1. A medicine dispensing pacifier comprising:

a flexible nipple, generally hollow and elongated with a bulbous end and an aperture in said bulbous end;

a guard, generally centering upon said nipple opposite said bulbous end, said guard permitting fluid communication from said nipple through said guard;

a reservoir connecting to said guard opposite said nipple, said reservoir having a wall and a generally round shape, the reservoir having an open end opposite to the guard, the reservoir adapted to contain medicine and being fluidly connected to the nipple; and a pump for compressing the medicine contained in the reservoir, the pump including a plunger with a cylindrical base having a gasket at one end and a convex cap at an opposite end, the base having a diameter similar to an inside diameter of the reservoir, the plunger being insertable into the reservoir so that the convex cap is positioned outside the reservoir and the gasket is positioned within the reservoir to prevent medicine in the reservoir from leaking out the open end, and wherein the cap is depressible to dispense the medicine through the aperture with an amount of pressure.

* * * * *